(12) United States Patent
Vicenzi

(10) Patent No.: US 11,090,065 B2
(45) Date of Patent: Aug. 17, 2021

(54) TARGETING SYSTEM FOR THE GUIDED INSERTION OF A GUIDE WIRE OR A BONE SCREW

(71) Applicant: Orthofix S.R.L., Bussolengo (IT)

(72) Inventor: Federico Vicenzi, Verona (IT)

(73) Assignee: Orthofix S.R.L., Verona (IT)

( * ) Notice: Subject to any disclaimer, the term of this patent is extended or adjusted under 35 U.S.C. 154(b) by 118 days.

(21) Appl. No.: 16/609,896

(22) PCT Filed: May 3, 2018

(86) PCT No.: PCT/EP2018/061366
§ 371 (c)(1),
(2) Date: Oct. 31, 2019

(87) PCT Pub. No.: WO2018/202782
PCT Pub. Date: Nov. 8, 2018

(65) Prior Publication Data
US 2020/0146733 A1    May 14, 2020

(30) Foreign Application Priority Data

May 4, 2017    (IT) .................. 102017000048427

(51) Int. Cl.
*A61B 17/86* (2006.01)
*A61B 17/17* (2006.01)
(Continued)

(52) U.S. Cl.
CPC .......... *A61B 17/17* (2013.01); *A61B 17/1796* (2013.01); *A61B 17/62* (2013.01);
(Continued)

(58) Field of Classification Search
CPC ..... A61B 17/17; A61B 17/1775; A61B 17/64; A61B 17/66
See application file for complete search history.

(56) References Cited

U.S. PATENT DOCUMENTS 2,181,746 A * 11/1939 Siebrandt ........... A61B 17/8866
  606/96
4,922,896 A *  5/1990 Agee .................. A61B 17/6425
  606/55
(Continued)

FOREIGN PATENT DOCUMENTS

FR    2674120 A1 * 9/1992 ............ A61B 17/60
FR    2674120 A1    9/1992
(Continued)

OTHER PUBLICATIONS

International Searching Authority / European Patent Office, "International Search Report," for PCT/EP2018/061366, dated Nov. 14, 2018, 7 pages.

*Primary Examiner* — Christian A Sevilla
(74) *Attorney, Agent, or Firm* — Haynes and Boone, LLP

(57) ABSTRACT

A targeting system (1) for the guided insertion of a guide wire (50) or a bone screw comprising: a stabilization body (2) fixed to the bone by means of stabilization screws (3); a guide sleeve (4) adapted to receive a guide cannula (5) for the insertion of the guide wire (50) or bone screw; articulated connection means (6) adapted to connect the stabilization body (2) to the guide sleeve (4) and allow the relative spatial position of the guide sleeve (4) to be varied with respect to the stabilization body (2).

4 Claims, 22 Drawing Sheets

(51) Int. Cl.
*A61B 17/62* (2006.01)
*A61B 17/88* (2006.01)
*A61B 17/64* (2006.01)
*A61B 17/00* (2006.01)

(52) U.S. Cl.
CPC .......... *A61B 17/64* (2013.01); *A61B 17/8625* (2013.01); *A61B 17/8897* (2013.01); *A61B 17/1775* (2016.11); *A61B 2017/00991* (2013.01)

(56) References Cited

U.S. PATENT DOCUMENTS

| | | | | |
|---|---|---|---|---|
| 5,454,810 | A * | 10/1995 | Pohl | A61B 17/6466 606/54 |
| 5,683,389 | A * | 11/1997 | Orsak | A61B 17/6425 606/54 |
| 6,355,036 | B1 * | 3/2002 | Nakajima | A61B 17/66 606/54 |
| 2002/0026190 | A1 * | 2/2002 | Walulik | A61B 17/66 606/57 |
| 2007/0083210 | A1 * | 4/2007 | Hestad | A61B 17/7002 606/86 R |
| 2008/0109085 | A1 | 5/2008 | Tulkis et al. | |
| 2009/0118733 | A1 | 5/2009 | Orsak et al. | |
| 2014/0012269 | A1 * | 1/2014 | Bass | A61B 17/64 606/90 |
| 2014/0114357 | A1 | 4/2014 | Hawkes et al. | |
| 2016/0038184 | A1 * | 2/2016 | Erickson | A61B 17/6416 606/59 |

FOREIGN PATENT DOCUMENTS

| | | |
|---|---|---|
| WO | WO 97/41790 A2 | 11/1997 |
| WO | WO 99/22661 A1 | 5/1999 |
| WO | WO 2004/45451 A2 | 6/2004 |
| WO | WO 2012/122317 A2 | 9/2012 |
| WO | WO 2016/039756 A1 | 3/2016 |
| WO | WO 2017/016611 A1 | 2/2017 |

* cited by examiner

TARGETING SYSTEM FOR THE GUIDED INSERTION OF A GUIDE WIRE OR A BONE SCREW

CROSS REFERENCE TO RELATED APPLICATIONS

The present application is the U.S. national phase of International Application No. PCT/EP2018/061366, filed May 3, 2018, which designated the U.S. and claims priority to and the benefit of the Italian Application No. 102017000048427, filed May 4, 2017, both of which are hereby incorporated by reference in their entirety as if fully set forth below in its entirety and for all applicable purposes.

FIELD OF THE INVENTION

The present invention relates to a targeting system, i.e. an orthopaedic instrument, for supporting the surgeon in the insertion of a guide wire or a bone screw in a specific point of the skeleton of a patient.

In particular, the invention can be usefully applied in the insertion of a guide wire for inserting a cannulated screw, for example into the bones of the foot of a patient, and the following description is done with non-limiting reference to the use in the context of that application.

PRIOR ART

In the technical field of the present invention, it is known to resort to bone screws intended for fracture reduction in various parts of the skeleton of a patient.

In order to insert the bone screw correctly and in the desired position, a guide wire is used inserted in advance in the position which the screw is to be inserted into. The bone screw is generally cannulated, i.e. it has an axial duct along the whole extension thereof for slidingly inserting the guide wire. In fact, once the guide wire is in position, the cannulated screw is let slide along the guide wire up to reach the bone surface and then screwed into the bone keeping on following the guide wire.

Once the screw insertion is concluded, the guide wire is removed.

In order to be able to control the direction and the correct positioning of the guide wire, the insertion procedure of the guide wire through the patient's soft tissues and bone is monitored by radioscopy of the implant area.

As a rule, the guide wire is equipped with a tip with a drilling profile.

The insertion procedure of the guide wire provides the use of a drill for perforating into the bone. The surgeon must thus hold the drill firmly in his hand in proximity to and approaching the implant site in order to ensure the correct positioning of the guide wire.

Although advantageous under various aspects, and essentially responding to the current needs of the field, the insertion procedure of the guide wire has nevertheless some drawbacks unsolved to date.

First, it is convenient to notice that the surgeon's hands are constantly subject to radioscopy x-rays during the insertion.

The insertion procedure has moreover some drawbacks related to the difficulties encountered by the surgeon in keeping the drill stability. In particular, the difficulties derive from the intrinsic weight of the drill that the surgeon must continuously support by his own hands. Accordingly, the drill is subject to more or less wide oscillations, transmitted by the surgeon's hands, which can compromise the accuracy in the guide wire positioning.

It was also possible to ascertain how the duration of the whole operation is more or less reduced depending on the surgeon's skill.

A further drawback is related to the guide wire size itself. In general, the guide wires used for implanting cannulated screws have a very high length with respect to the cross section having a diameter of a few millimeters at most. During the insertion, the guide wire is thus susceptible of bending due to the peak load applied with the drill. That bending can determine some errors in directing the guide wire which risks being inserted in a wrong position and thus having to be removed in order to be inserted again.

A wrong positioning of the screw resulting from an error in the guide wire positioning can determine a wrong treatment of the patient.

A solution adopted to support a surgeon in the insertion of a bone perforating element is provided by the apparatus shown in FIG. 55 of document WO 2012/122317 A2.

Said apparatus includes a stabilization body fixed to a long bone by means stabilization pins and a guide passageway configured to receive a wire support. Articulated connection means adapted to connect said stabilization body to said guide passageway allow relative spatial position of the guide passageway to be varied with respect to said stabilization body.

Though advantageous under various aspects and substantially responding to the purpose, this solution provides a reduced flexibility in positioning of the wire support that could be oriented just in a limited number of spatial positions relative to the stabilization body. Indeed, the apparatus of FIG. 55 of WO 2012/122317 A2 does not allow to insert a guide wire and/or a bone screw in a direction parallel to the longitudinal axis of the bone.

Furthermore, the apparatus discussed above allows to insert the stabilization pins with a fixed distance therebetween and thus it does not allow to reduce and align at least two bone fragments of a fracture after that the stabilization pins have been already inserted into the bone.

The technical problem underlying the present invention is to provide a targeting system for the guided insertion of a guide wire which allows prior art drawbacks to be overcome, and particularly the surgeon to be supported, allowing times to be reduced and the accuracy of insertion of a guide wire in any anatomical site of a patient to be increased.

SUMMARY OF THE INVENTION

The above-mentioned technical problem is solved by a targeting system for the guided insertion of a guide wire or a bone screw, in accordance with claim 1 of the present invention.

The dependent claims define particularly advantageous embodiments of the targeting system according to the invention.

Further features and advantages will be more apparent from the following detailed description of preferred, but not exclusive, embodiments of the present invention, with reference to the attached figures, given by way of non-limiting examples.

DETAILED DESCRIPTION OF THE PREFERRED EMBODIMENTS

With reference to those figures, a preferred embodiment of the targeting system for supporting the surgeon during the insertion of a guide wire for cannulated bone screw in any anatomical site of the skeleton of a patient is globally and schematically indicated with 1. This does not exclude that the targeting system can be used directly for inserting a bone screw as an alternative to the guide wire.

The targeting system 1 of the present invention is particularly adapted, although not exclusively, to the guided insertion of a guide wire at the bones of the foot of a patient. The following description is done with non-limiting reference to the use in the context of that application.

Figure 1:
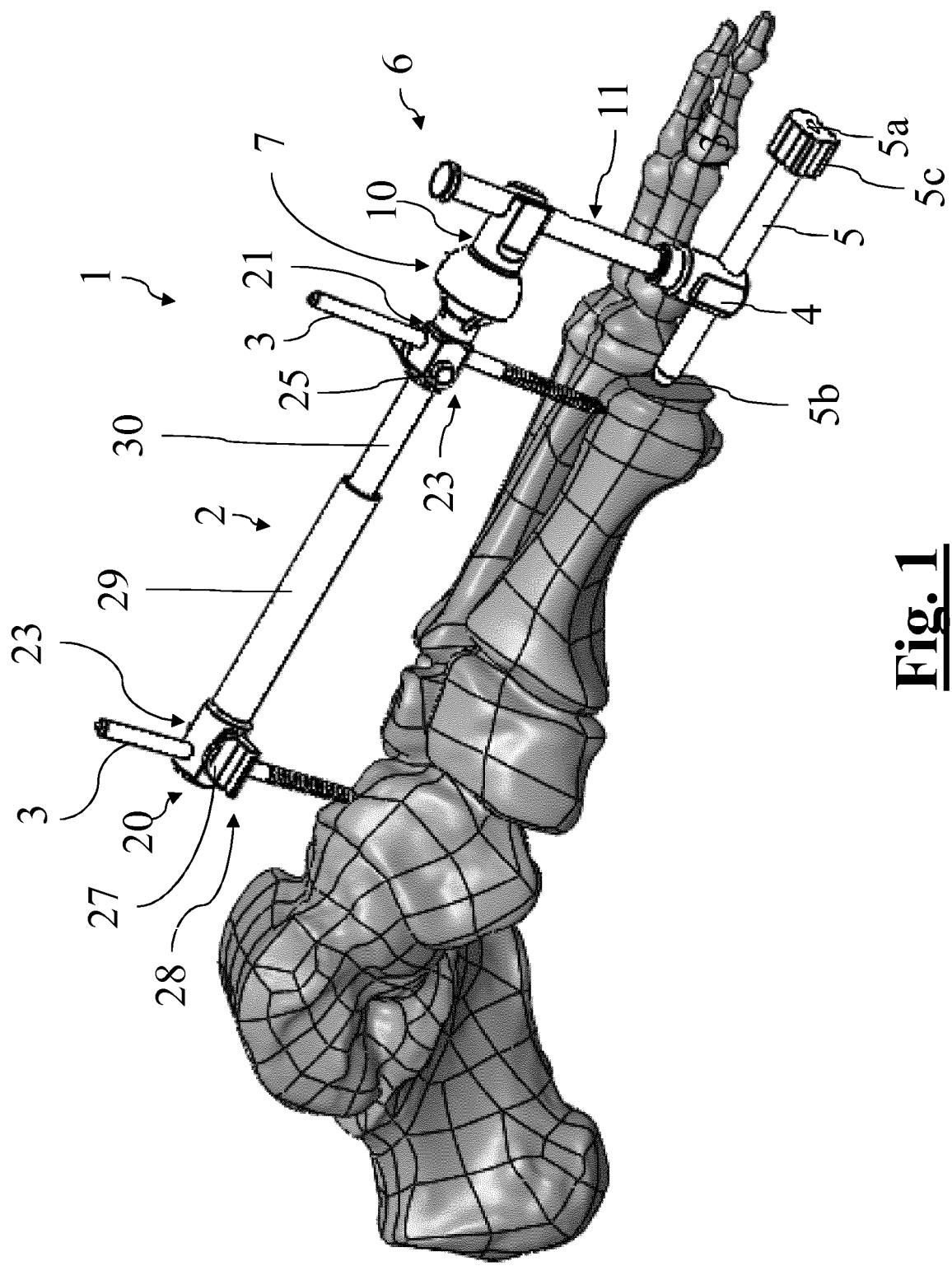
FIG. 1 shows a perspective view of a first embodiment of the targeting system according to the present invention applied to a skeletal model of a patient's foot.
Figure 2:
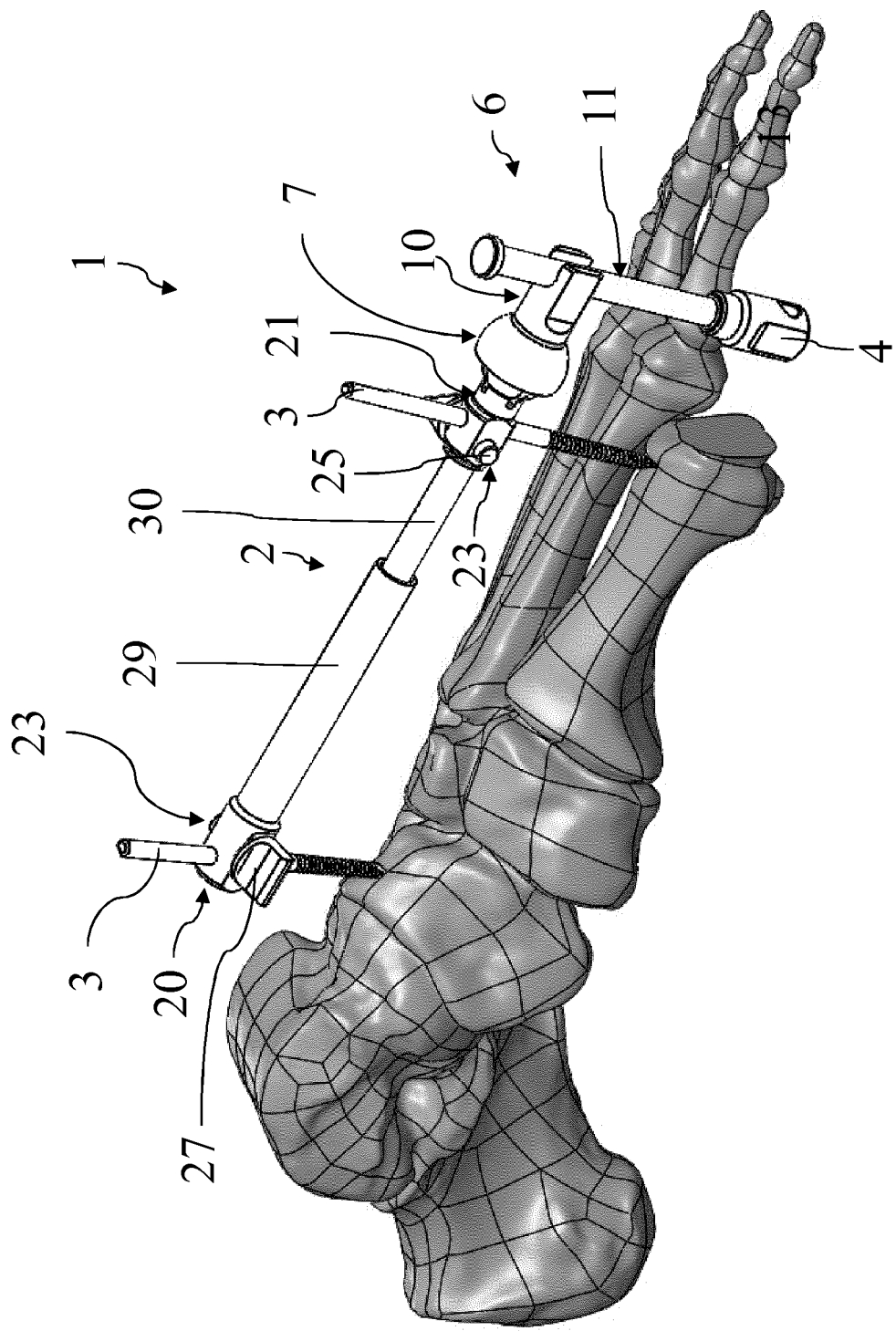
FIG. 2 shows a perspective view of the targeting system of FIG. 1, without guide cannula inserted, applied to a skeletal model of a patient's foot.

FIG. 1 shows in fact a preferred embodiment of the targeting system 1 applied to a foot skeletal model.

That targeting system 1 consists of a surgical instrument which can be stabilized to the bone with stabilization screws 3 and which allows, through the manual adjustment of articulated connection means 6, a guide cannula 5 for the insertion of a guide wire 50 to be positioned at a specific point of the bone.

In a preferred embodiment, the targeting system 1 comprises a stabilization body 2 which has a telescopic structure. The stabilization body 2 has, at a first 20 and second 21 end, an insertion hole 22, having an insertion hole axis Z, for the insertion of a stabilization screw 3 and locking means 23 of the stabilization screw 3. The telescopic structure allows the two ends 20, 21, i.e. the stabilization screws 3 housed therein, to be moved away/approached or rotated with respect to each other, before both stabilization screws 3 are fixed to the bone.

In a preferred embodiment, the stabilization screws 3 are self-drilling.

An articulated ball joint 7 defined by the coupling of a spherical male element 8, fixed to the second end 21 of the stabilization body 2, and of a spherical seat 9 is positioned at the second end 21 of the stabilization body 2.

The spherical seat 9 has a base 9a which a guide clamp 10 is fixed to. The articulated joint 7 allows relative angular movements of the guide clamp 10 with respect to the second end 21 of the stabilization body 3.

The guide clamp 10 has a pair of parallel arms 12 which encompasses a connection rod 11 free to translate and rotate about its own rod axis X.

A guide sleeve 4 having a sleeve axis Y orthogonal to the rod axis X is located at an end of the connection rod 11. The guide cannula 5, which is free to move with respect to the guide sleeve 4 rotating about and/or translating along the sleeve axis Y, is coaxially inserted into the guide sleeve 4.

The articulated joint 7 and the connection rod 11 coupled to the guide clamp 10 form the articulated connection means 6 which allow the relative spatial position of the guide sleeve 4, and thus of the guide cannula 5 inserted therein, to be manually adjusted with respect to the stabilization body 3 suitably fixed to the bone. That manual adjustment can be performed by rotating the spherical male element 8 within the spherical seat 9 and by rotating and/or translating the connection rod 11 with respect to the guide clamp 10.

In the following description the technical and functional features of the above-mentioned components of the targeting system 1 will be further investigated.

Figure 14:
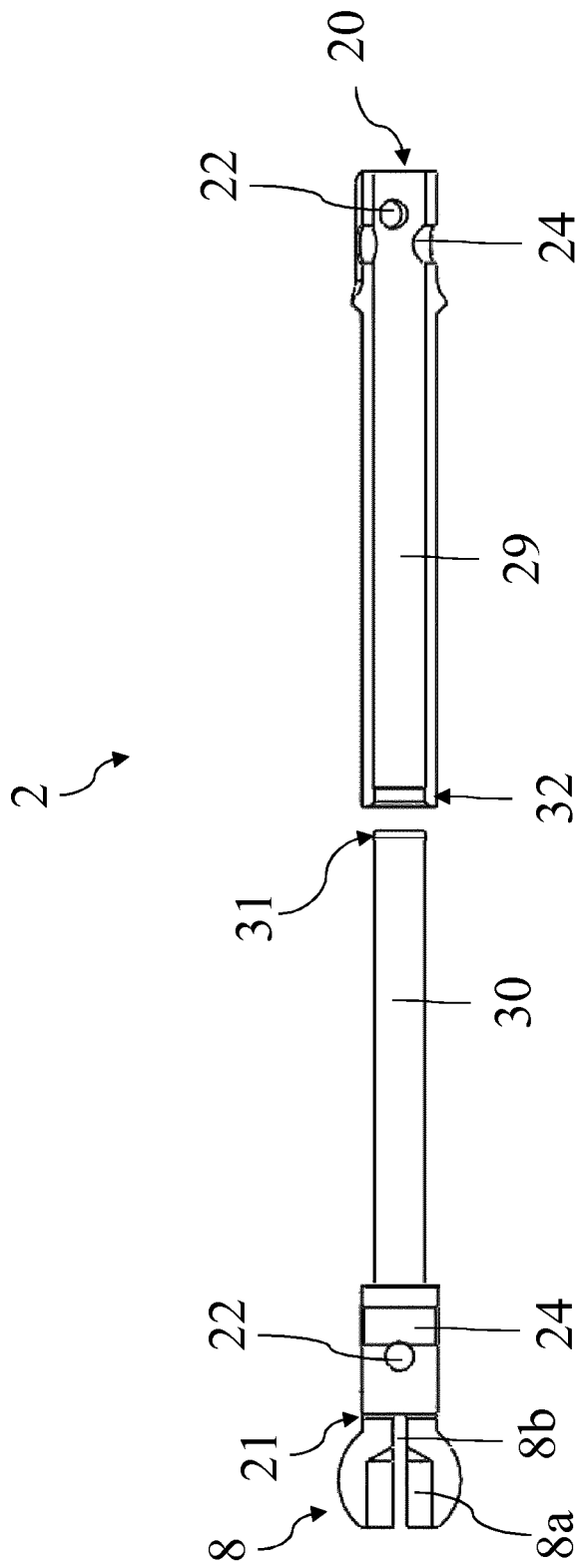
FIG. 14 shows a cross-sectional view of the stabilization body of the targeting system of FIG. 1, with the cylindrical element decoupled from the tubular guide element.

The locking means 23, present at both ends 20, 21 of the stabilization body 2, comprise a locking through hole 24 having a locking hole axis B orthogonal to the insertion hole axis Z. In other words, the locking hole 24 extends orthogonally to the insertion hole 22 housing the stabilization screw 3 and it further appears to be partially confluent therein (see FIG. 14).

The locking means 23 further comprise a locking element 28 which is defined in turn by an essentially cylindrical bar 25, and by a handle 27 formed as a single piece at one end of the bar 25. The handle 27 allows the bar 25 to be coaxially introduced and rotated about its own axis into the locking hole 24. The bar 25 has a transverse flattening 26, extended along the bar and lying on a plane parallel to the locking hole axis B when the bar 25 is inserted in the locking hole 24. That flattening 26 defines a chord of the circular section of the bar 25. The flattening 26 is thus formed starting from a cylindrical bar by removing a part of the material so as to locally reduce the resistant section of the bar.

Figure 19:
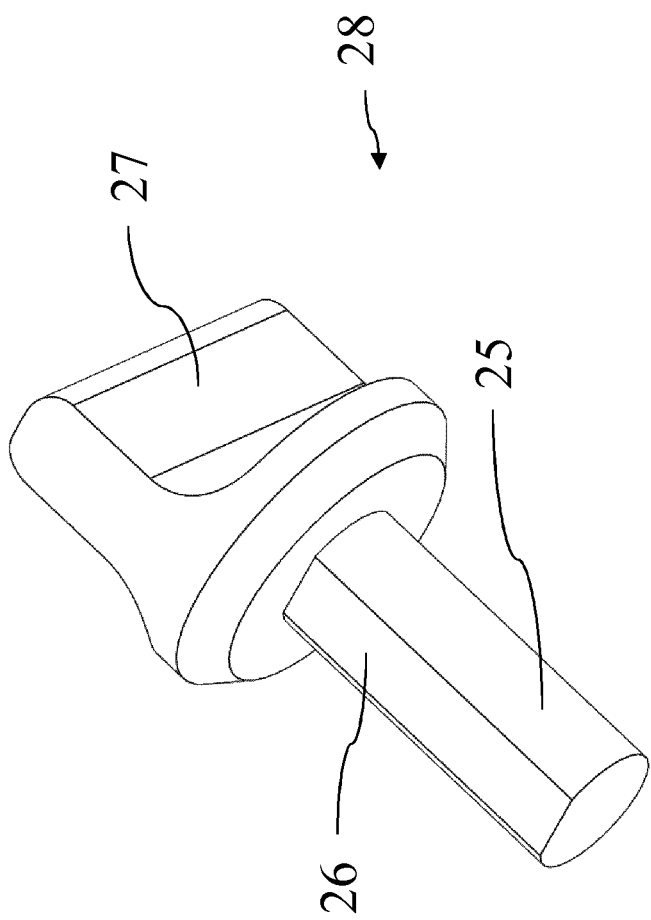
FIG. 19 shows a perspective view of a locking element of the targeting system of FIG. 1.

FIG. 19 shows a perspective view of the single locking element 28.

Figure 16:
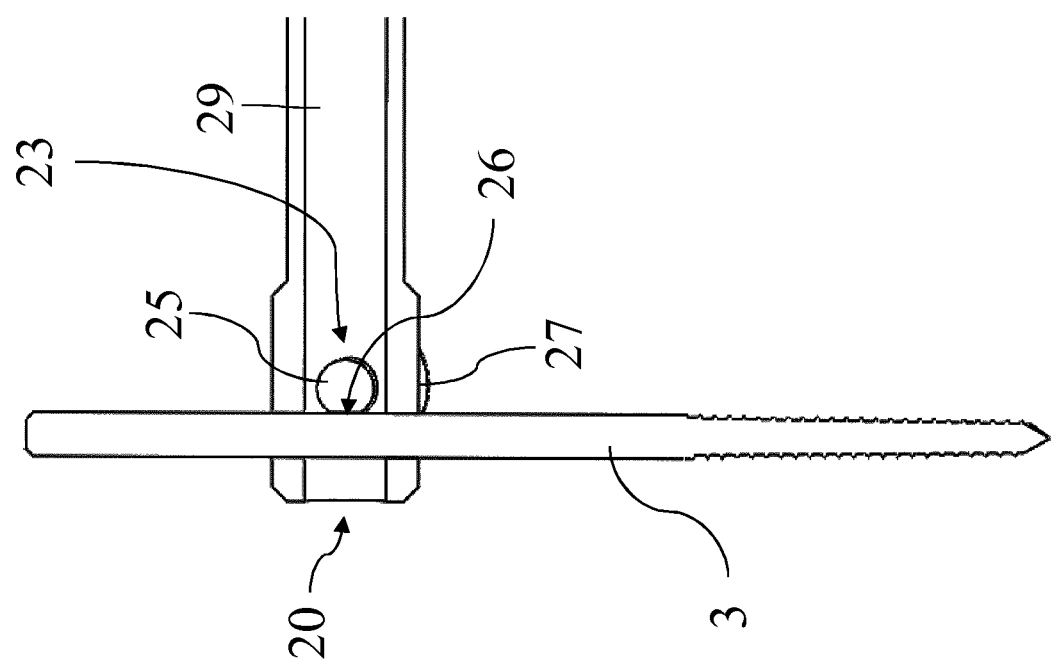
FIG. 16 shows a cross-sectional view of a detail of the targeting system of FIG. 1 with the locking means in a screw sliding configuration.
Figure 17:
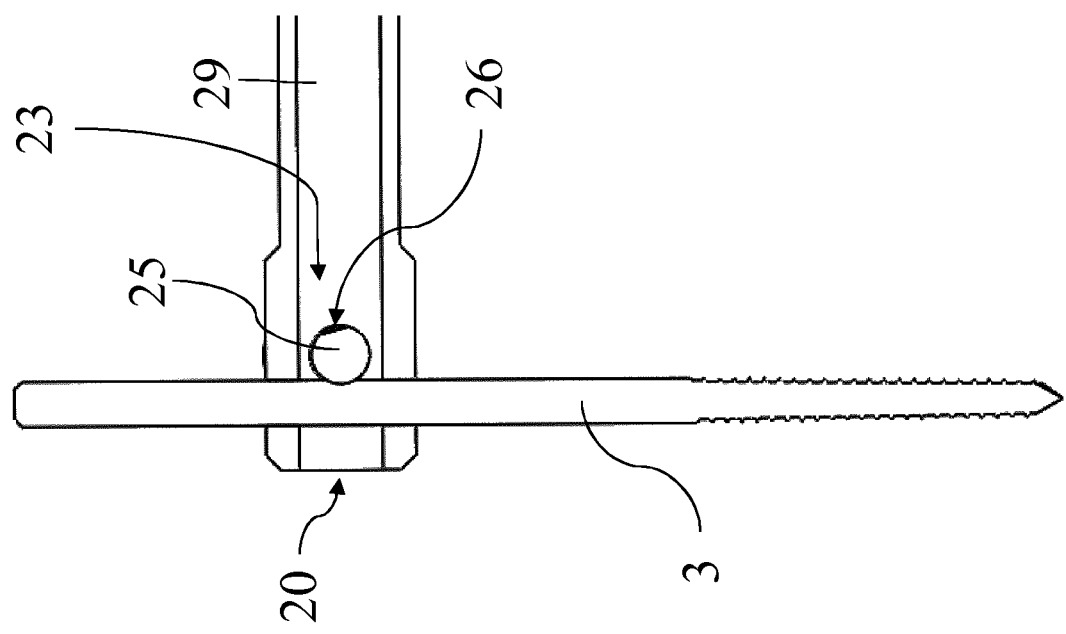
FIG. 17 shows a cross-sectional view of a detail of the targeting system of FIG. 1 with the locking means in a screw locking configuration.
Figure 18:
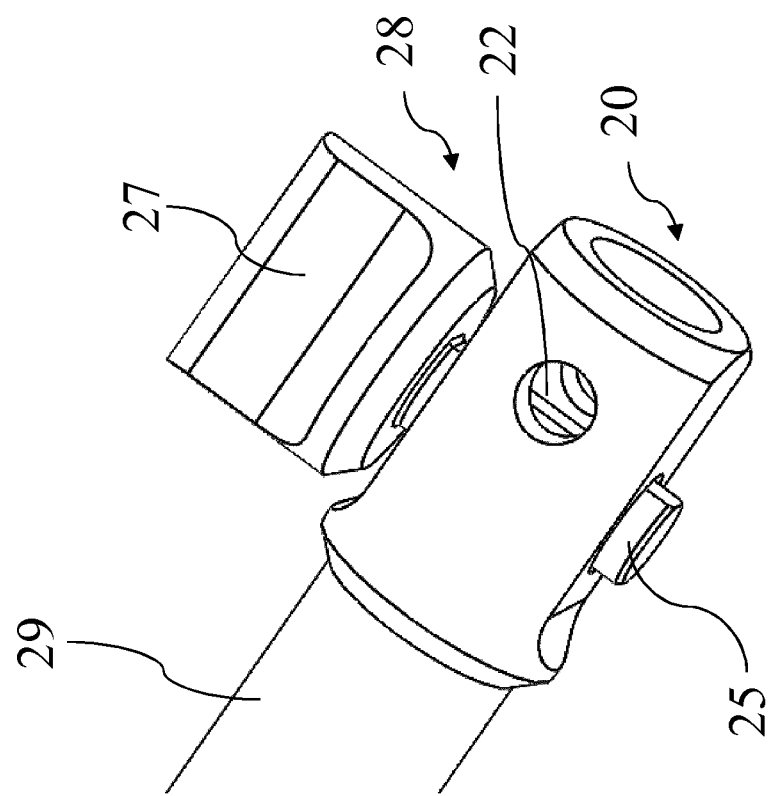
FIG. 18 shows a perspective view of a detail of the targeting system of FIG. 1 with the locking means in a screw sliding configuration.

The locking means 23 are characterized by two possible alternative configurations: a screw sliding configuration (FIGS. 16 and 18) and a screw locking configuration (FIG. 17). As it can be noticed in FIGS. 16 and 18, in the screw sliding configuration, the bar 25 of the locking element 28 is introduced into the locking hole 24 so that the flattening 26 is parallel to the insertion hole axis Z and facing the stabilization screw 3 inserted in the insertion hole 22. In that configuration the locking element 28 and the stabilization screw 3 are free to axially slide within the locking hole 24 and the insertion hole 22 respectively. The locking means 23 in a screw locking configuration are instead represented in FIG. 17, the bar 25 of the locking element 28 appears to be rotated with respect to the screw sliding configuration and it locks by interference the stabilization screw 3, which is no more free to slide. It can be noticed that the flattening 26 must be conveniently sized so that when the locking means 23 are in the screw sliding configuration, the bar 25 does not occupy the insertion hole 22; which occurs on the contrary when they are in the screw locking configuration, wherein a stabilization eccentric effect is performed, which, due to the interference, locks the axial movements of the locking element 28 and of the stabilization screw 3 within the respective holes 24, 22.

The stabilization body 2 is represented in FIGS. 12-15, particularly emphasizing the telescopic structure, in a decoupled configuration.

That telescopic structure comprises a tubular guide element 29, delimited on one side by the first end 20 of the stabilization body 2 and on the other side by an entrance 32, and a cylindrical element 30, delimited on one side by the second end 21 of the stabilization body 2 and on the other side by an insertion end 31.

The cylindrical element 30 is sized so as to be able to be axially introduced into the tubular guide element 29 and to be able to perform relative movements therewithin, such as the axial translation and the rotation about its own axis.

The telescopic structure allows the stabilization body 2 to vary the length thereof, i.e. the distance between the first 20 and the second 21 end, i.e. between the stabilization screws 3. In the preferred embodiment of the present invention, the cylindrical element 30 has a length essentially equal to the length of the tubular guide element 29. The length of the stabilization body 2 can be thereby varied between a minimum in which the cylindrical element 30 is completely inserted within the tubular guide element 29 and a maximum in which the cylindrical element 30 is almost completely outside the tubular guide element 29. On the contrary, by rotating the cylindrical element 30 with respect to the tubular guide element 29 it is possible to vary the relative angular distance between the stabilization screws 3.

Figure 15:
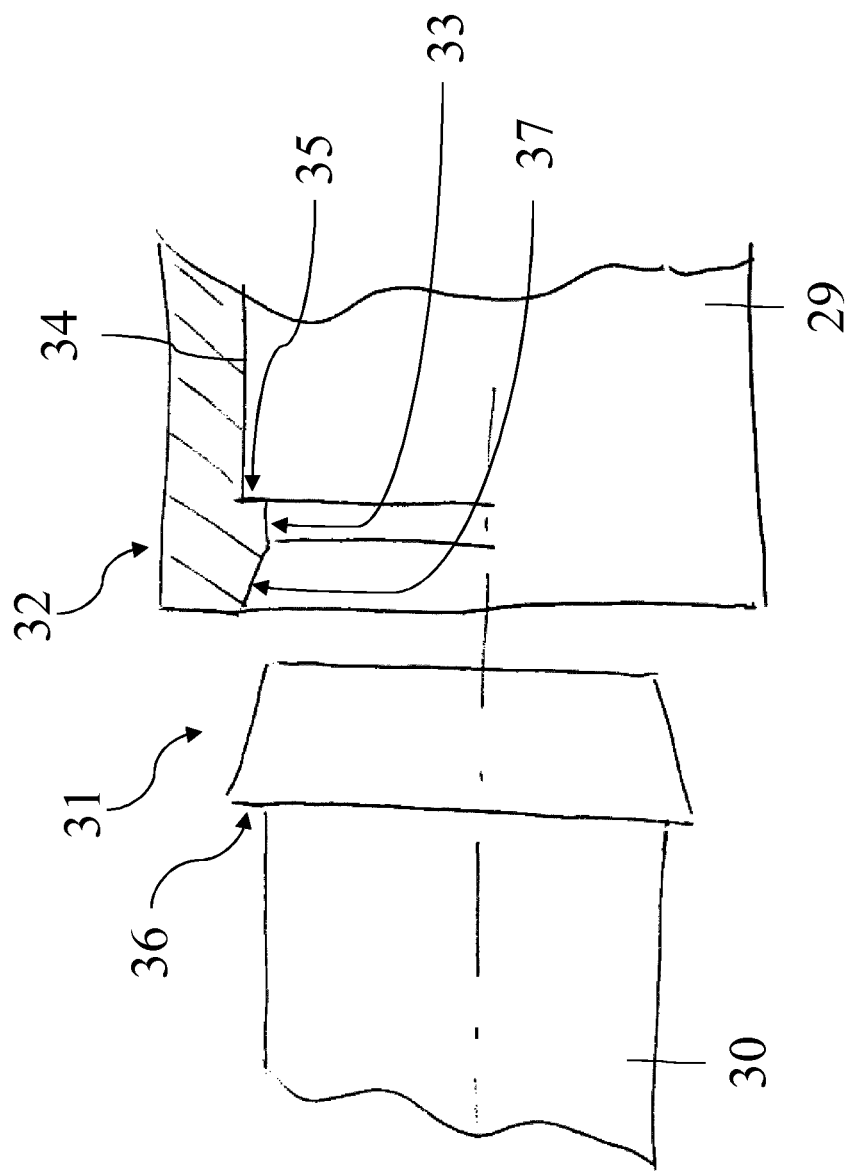
FIG. 15 shows a cross-sectional view of a detail of the stabilization body of the targeting system of FIG. 1, with the cylindrical element decoupled from the tubular guide element.

As pointed out in the detail of FIG. 15, the coupling between the cylindrical element 30 and the tubular guide element 29 provides a system for preventing the two elements from decoupling.

In particular, the entrance 32 of the tubular guide element 30 has a projection 33 of the inner wall 34 which determines a local reduction of the inner diameter of the tubular guide element 30. The projection 33 is jointed to the inner wall 34 by means of a stop surface 35. The entrance 32 has moreover a sloping surface 37 starting from the projection 33 away from the stop surface 35 and from the axis of the tubular guide element 30.

The insertion end 31 of the cylindrical element 30 has a shoulder 36 which determines a localized increase in the diameter of the cylindrical element 30. Starting from the shoulder 36, the insertion end 31 has a tapered trend away from the first end 20.

The assembly of the two elements 29, 30 of the telescopic structure occurs by press-fitting the insertion end 31 into the entrance 32. The slope of the sloping surface 37 of the entrance 32 is sized so as to facilitate the sliding of the tapered insertion end 31 thereon up to overcome the projection 33. Once the two elements 29, 30 are coupled, the shoulder 36 is sized so as to prevent the cylindrical element 30 from unthreading from the tubular guide element 29. In fact, if a sufficiently high force is not applied, in case the user tries to unthread the cylindrical element 30, once the limit stop is reached, the shoulder 36 arranges in abutment against the stop surface 35 resisting to decoupling.

With particular reference to FIGS. 6-9, the articulated ball joint 7 is now described in detail. As it can be noticed in FIG. 7, the spherical male element 8 has just a spherical shape and it is fixed to the second end 21 of the stabilization body 2. An axial recess 8a is drawn in the spherical male element 8 creating an essentially cylindrical recess tapered when approaching the second end 21. In other words, the spherical male element 8 is defined by a spherical shell which has an opening opposite to the second end 21. The spherical shell continuity is disjoined by four notches 8b which cross the spherical male element 8 leading in the axial recess 8a and are drawn by removing a specific thickness of material along two orthogonal planes which intersect at the ball axis. The presence of the axial recess 8a and of the notches 8b gives to the spherical male element 8 a radial elastic deformability, which, as it will be apparent hereafter, allows a firm coupling with the spherical seat 9 to be ensured.

Figure 8:
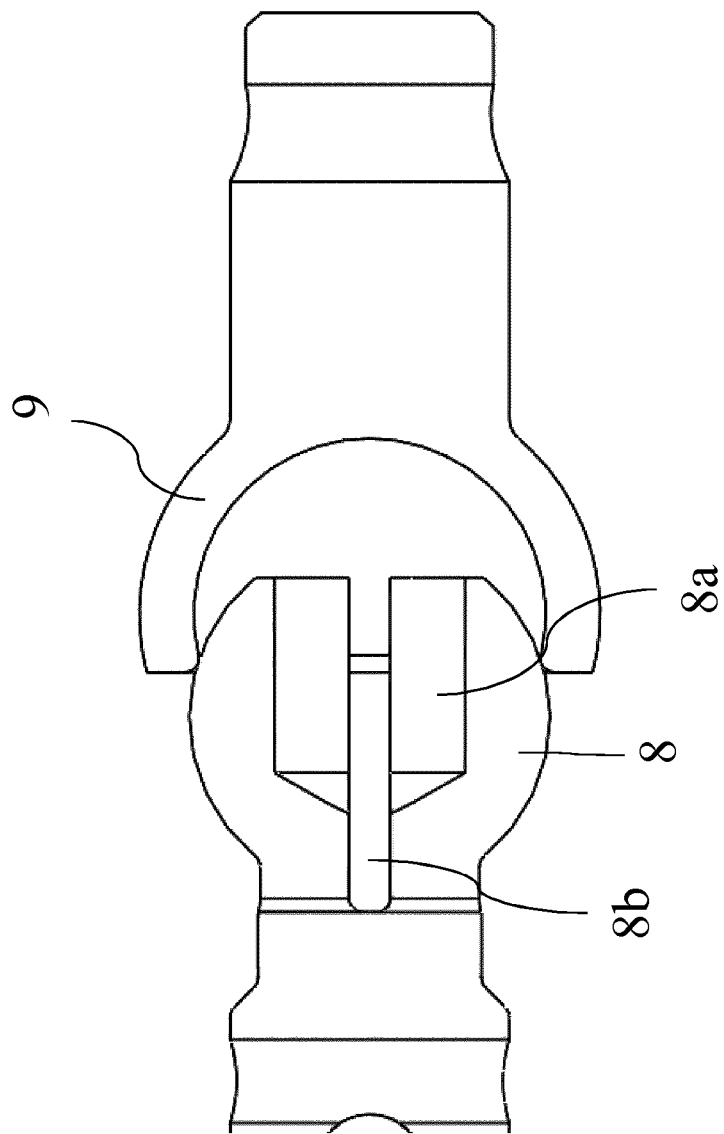
FIG. 8 shows a cross-sectional view of the articulated joint of FIG. 6, in a decoupled configuration.

FIG. 8 shows the spherical male element 8 and the spherical seat 9 of the articulated joint 7 in a decoupled configuration. As it can be noticed from FIG. 8, the male element 8 has an outer diameter larger than the inner diameter of the spherical seat 9.

The coupling of the spherical male element 8 with the spherical seat 9 is enabled by the presence of the notches 8b. In fact, when the spherical male element 8 is forced into the spherical seat 9, the spherical male element 8 undergoes a radial compression which determines a reduction of the width of the notches 8b with subsequent reduction of the outer diameter. That radial compression allows the spherical male element 8 to be completely inserted into the spherical seat 9. Once the spherical male element 8 is completely inserted, it will tend to open again as a result of the elastic return ensuring a firm coupling by interference. The coupling by interference is such as to allow the relative angular rotation of the spherical male element 8 with respect to the spherical seat 9 with friction between the contact surfaces.

Figure 6:
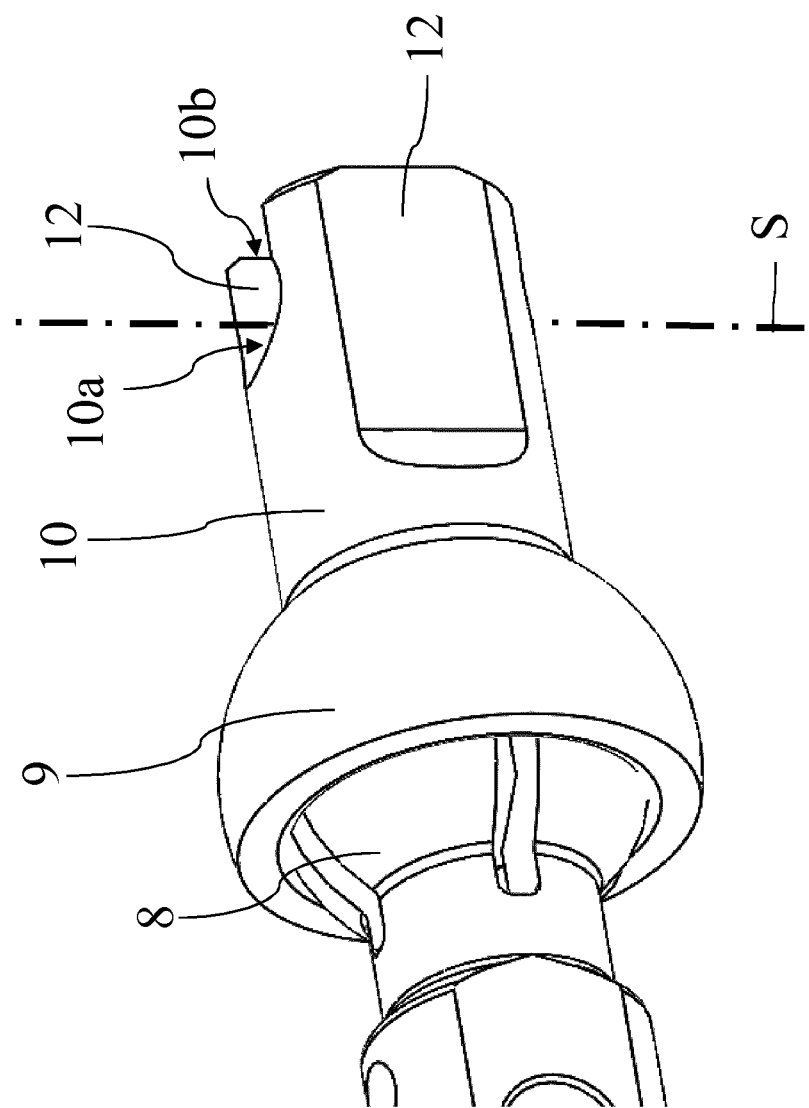
FIG. 6 shows a perspective view of the articulated joint in a coupled configuration.
Figure 7:
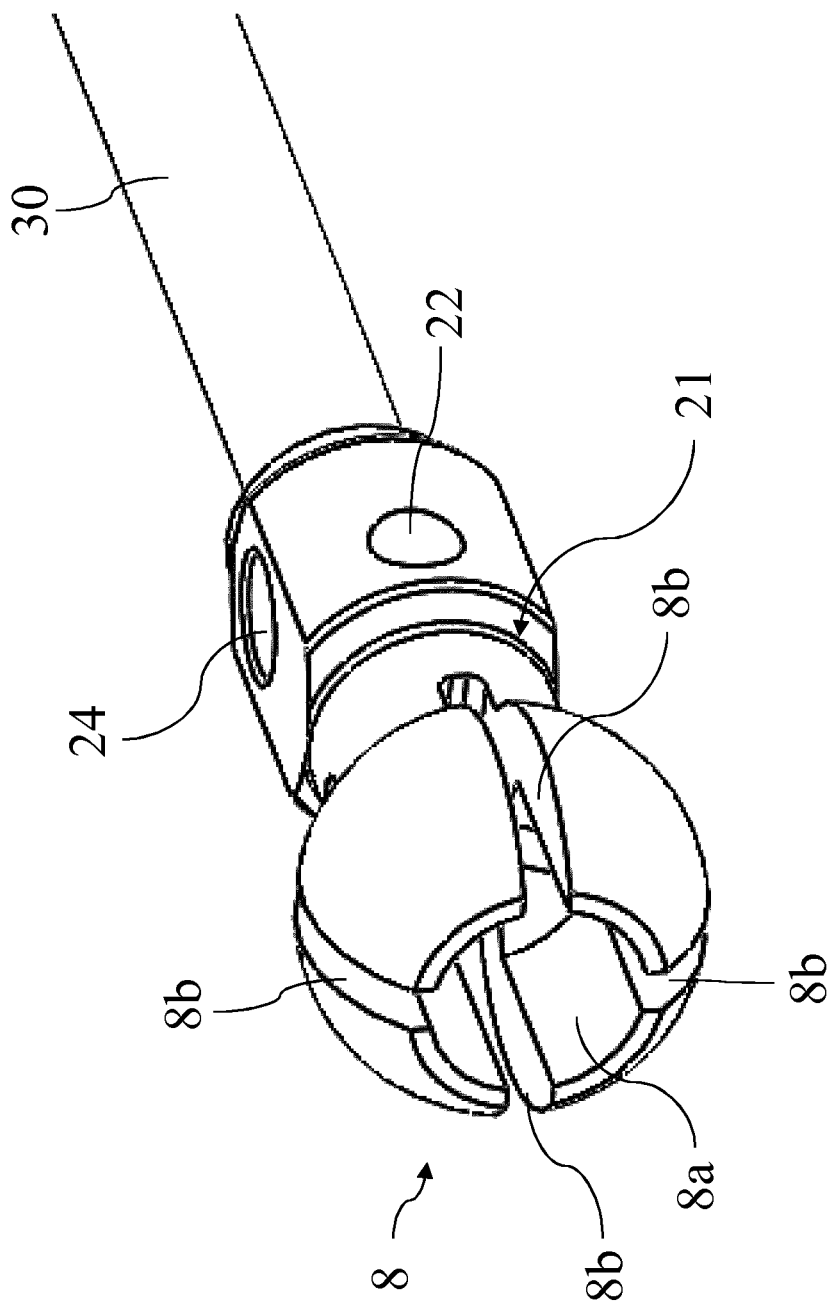
FIG. 7 shows a perspective view of the spherical male element of the articulated joint of FIG. 6 in a decoupled configuration.
Figure 9:
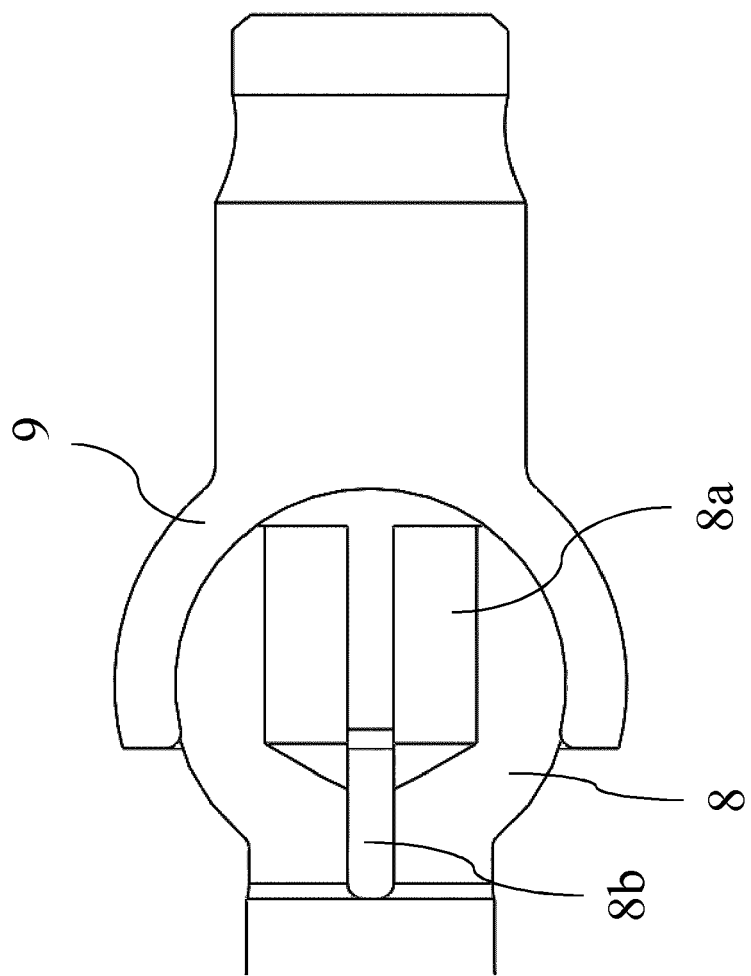
FIG. 9 shows a cross-sectional view of the articulated joint of FIG. 6, in a coupled configuration.

FIGS. 6 and 9 show the spherical male element 8 and the spherical seat 9 of the articulated joint 7 in a coupled configuration.

Differently-conceived joints can be used in alternative embodiments.

As mentioned above, the base 9a of the spherical seat 9 is fixed to the guide clamp 10. Referring in particular to FIGS. 4, 5, 10 and 11, it can be noticed that the guide clamp 10 comprises a cylindrical seat 10a having a cylindrical seat axis S. The cylindrical seat 10a comprises a cylindrical seat entrance 10b which enlarges the cylindrical seat 10a away from the spherical seat 9. The entrance 10b is delimited by a pair of parallel and elastic arms 12.

The connection rod 11, coupled to the guide clamp 10, has a cylindrical central portion 11b having a slightly lower diameter than the diameter of the cylindrical seat 10a which it can be coupled to and higher than the distance between the arms 12. The connection rod 11 has moreover at an end a head 11a with a larger diameter than the diameter of the cylindrical seat 10a. At the end opposite to the head 11a the guide sleeve 4 is instead located, having a sleeve axis Y orthogonal to the rod axis X. In a preferred embodiment the guide sleeve 4 is made as a single piece with the connection rod 11 so as to be able to move integrally therewith.

Figure 10:
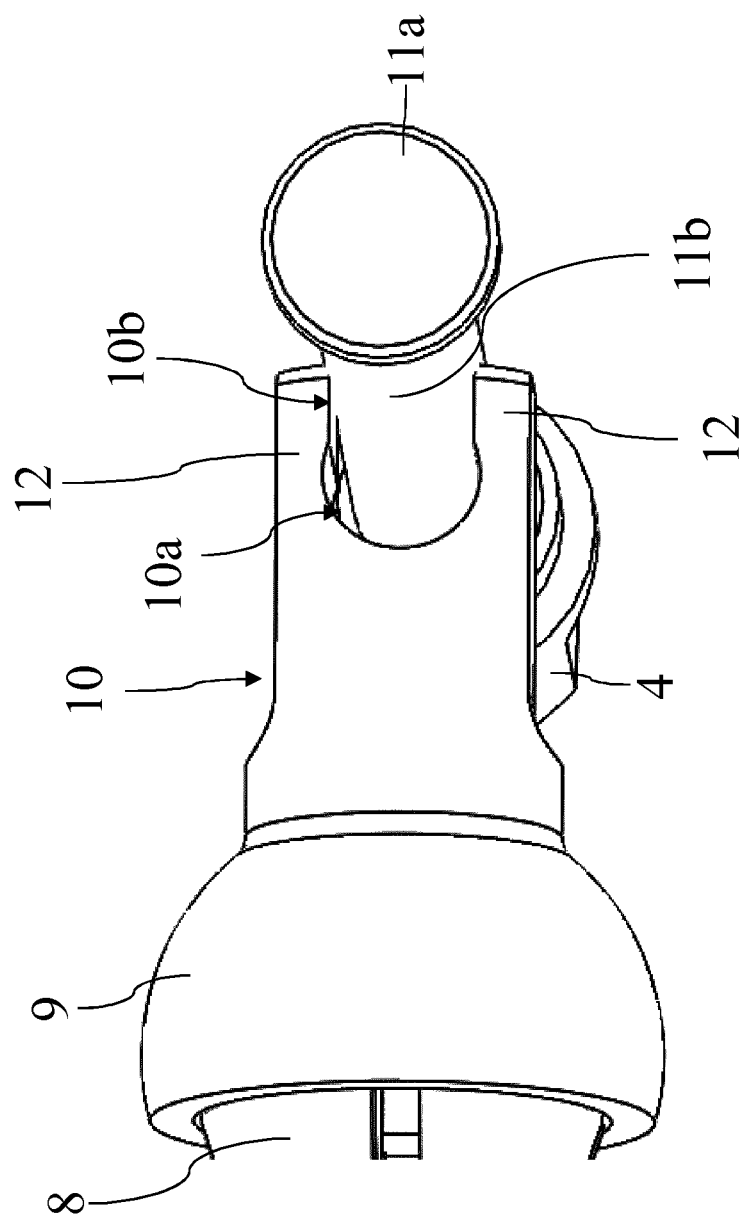
FIG. 10 shows a top perspective view of the guide clamp and of the connection rod of the targeting system of FIG. 1, in a decoupled configuration.
Figure 11:
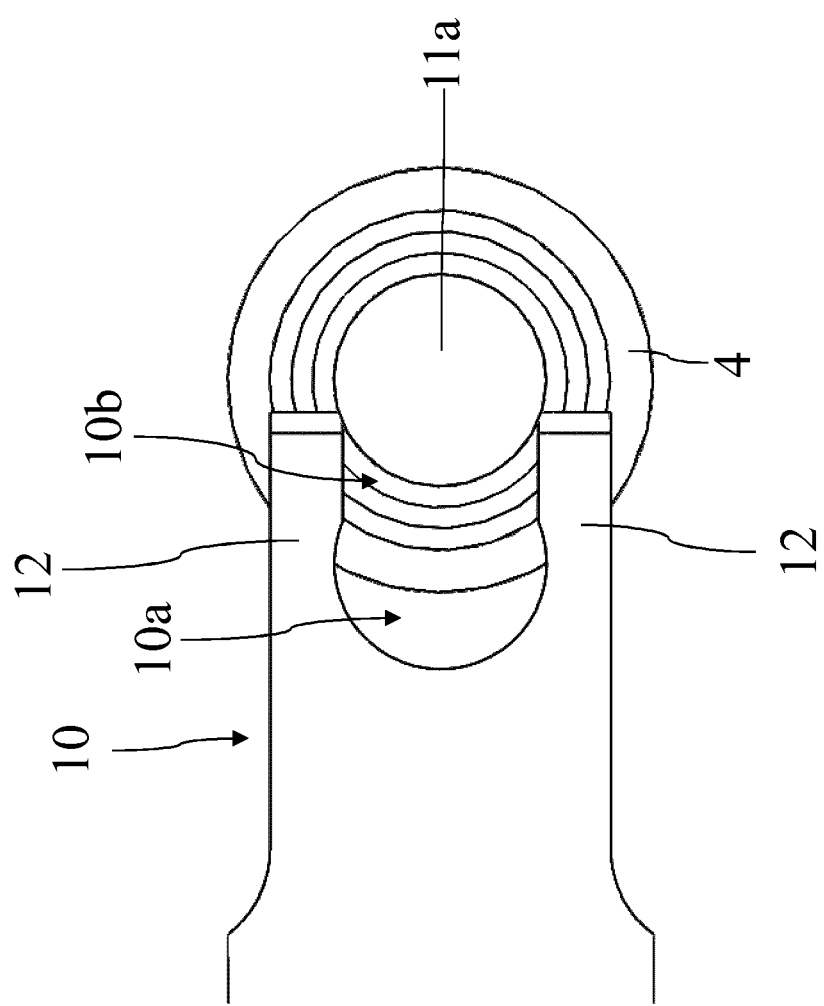
FIG. 11 shows a top view of the guide clamp and of the connection rod of the targeting system of FIG. 1, in a decoupled configuration.
Figure 12:
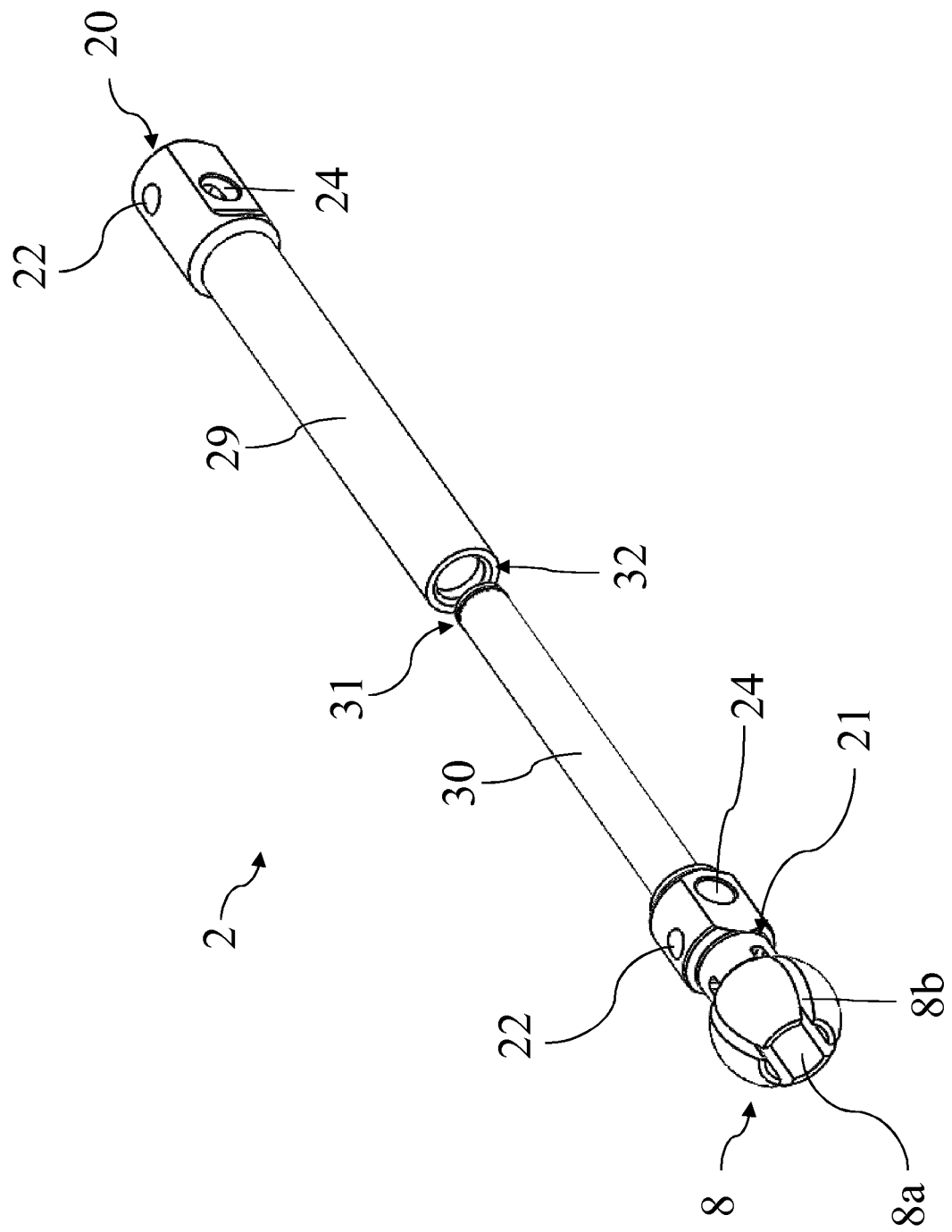
FIG. 12 shows a perspective view of the stabilization body of the targeting system of FIG. 1, with the cylindrical element decoupled from the tubular guide element.
Figure 13:
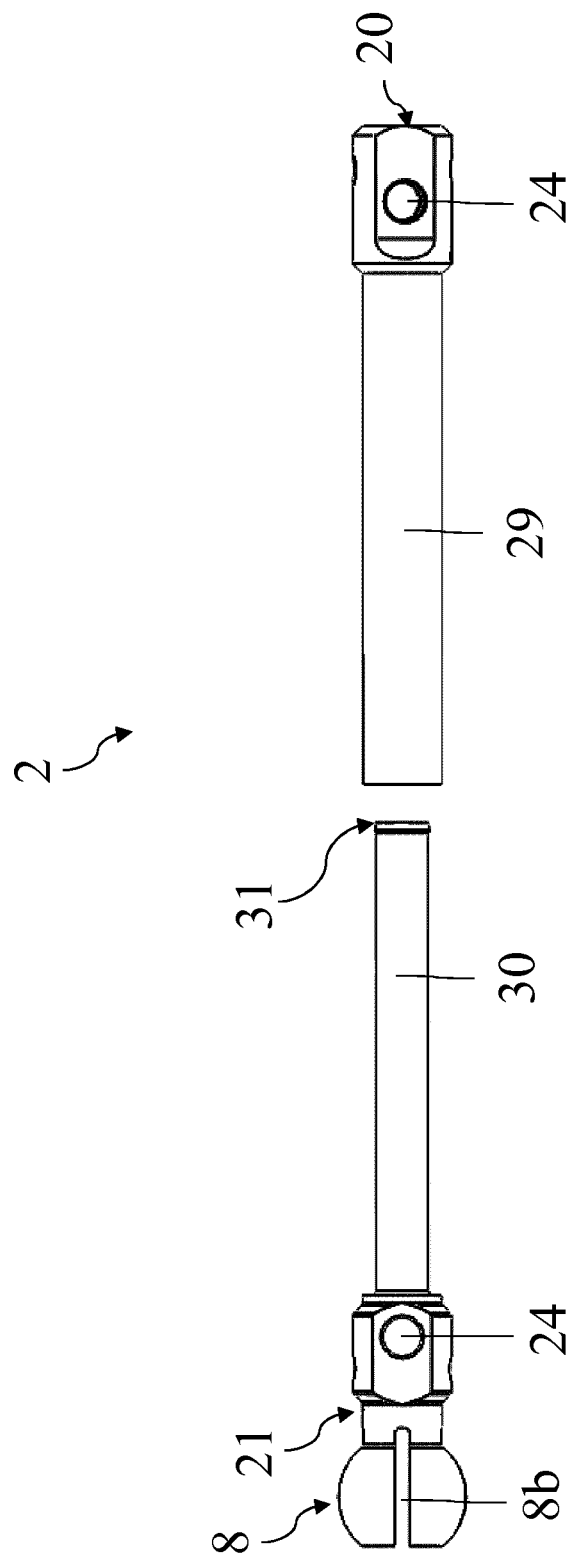
FIG. 13 shows a side view of the stabilization body of the targeting system of FIG. 1, with the cylindrical element decoupled from the tubular guide element.

FIGS. 10 and 11 show the guide clamp 10 and the connection rod 11 in a decoupled configuration. The coupling is performed by snap-fitting the central portion 11b of the connection rod 11 into the cylindrical seat entrance 10b, keeping the rod axis of the rod X parallel to the cylindrical seat axis S. During coupling, the arms 12 elastically open allowing the connection rod 11 to enter the cylindrical seat 10a. Once the connection rod 11 is inserted, the arms 12 tend to approach each other again keeping the connection rod 11 within the cylindrical seat 10a.

FIGS. 1-5 show the connection rod 11 coupled to the guide clamp 12. The connection rod 11 is free to slide with friction of the contact surfaces with respect to the cylindrical seat 10a. In particular, the connection rod 11 can translate along and rotate about the direction identified by the cylindrical seat axis S. The head 11a and the guide sleeve 4 located at the ends of the connection rod 11 define the translation limit stop abutting against the pair of arms 12.

Figure 3:
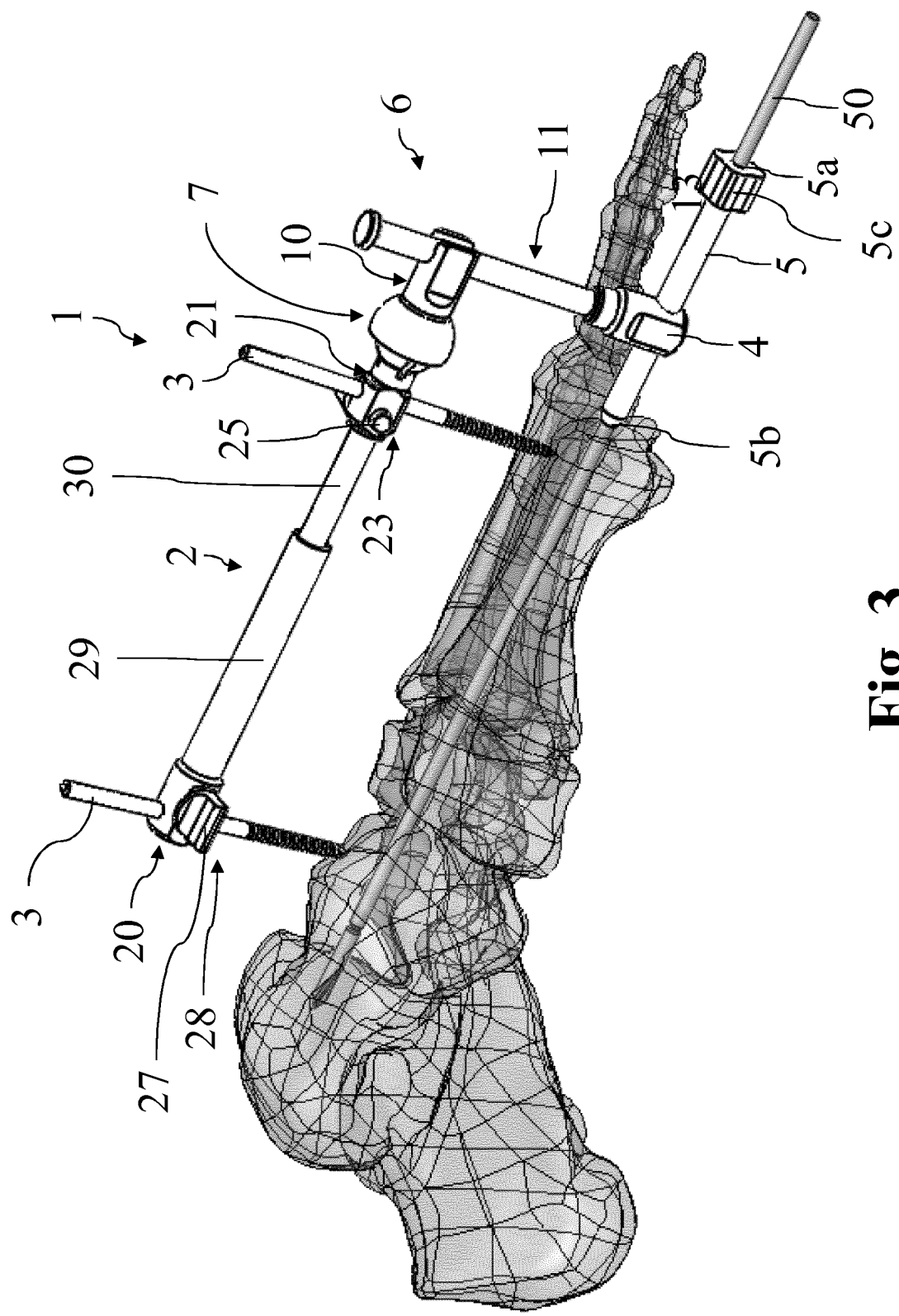
FIG. 3 shows a perspective view of the targeting system of FIG. 1 applied to a skeletal model of a patient's foot, with the guide wire inserted into the bone.
Figure 4:
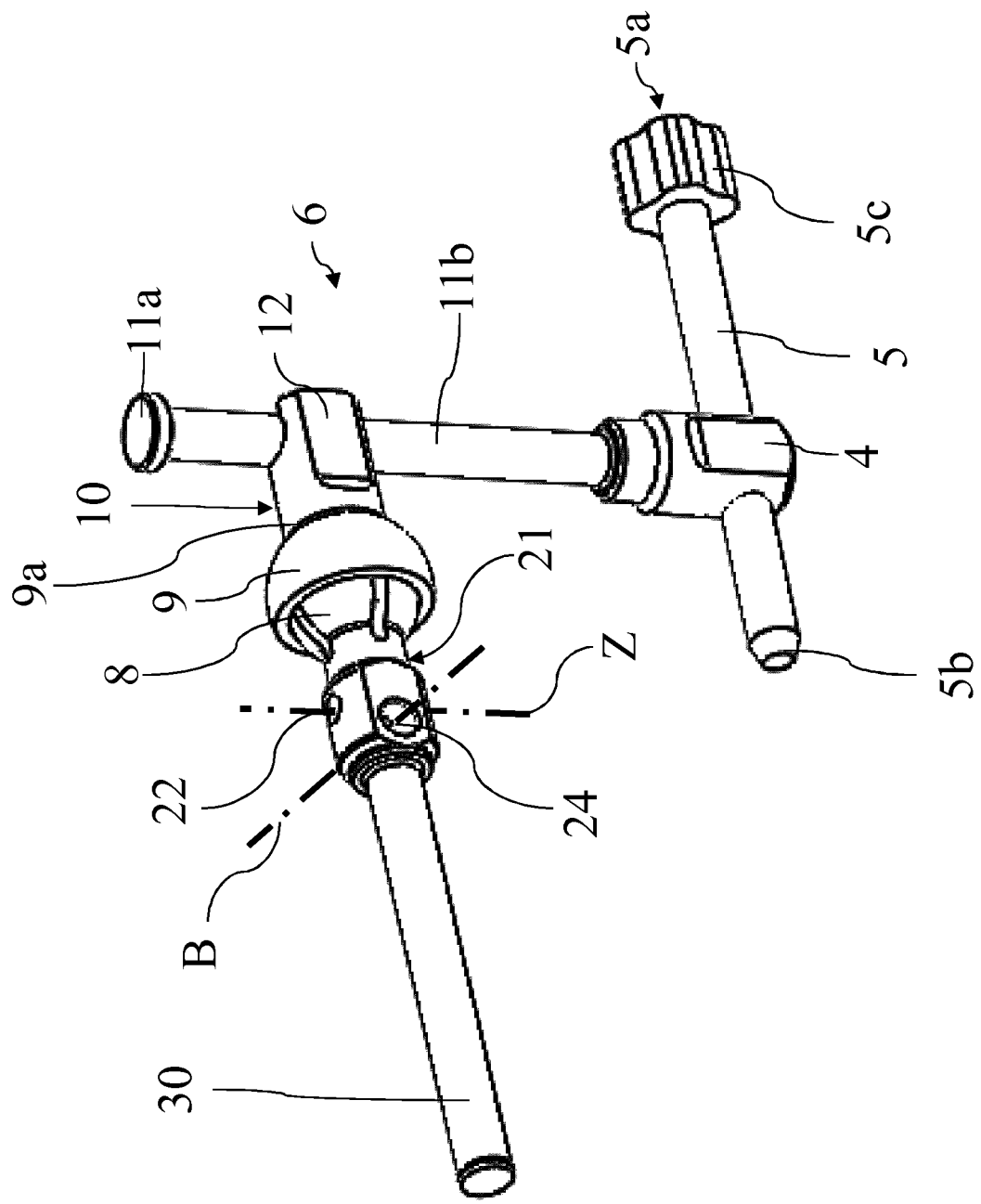
FIG. 4 shows a perspective view of a part of the targeting system of FIG. 1.
Figure 5:
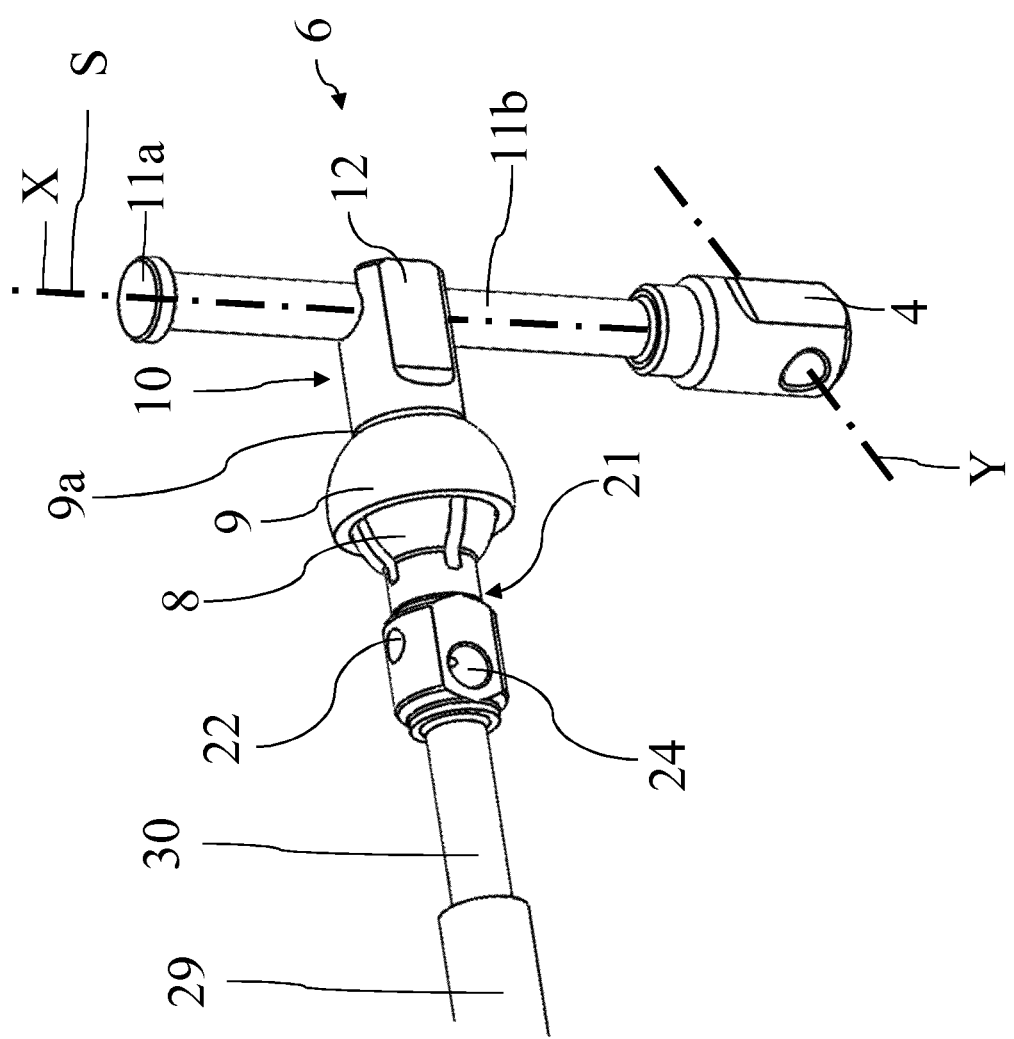
FIG. 5 shows a perspective view of a part of the targeting system of FIG. 1, without guide cannula inserted.

As it can be noticed in particular from FIGS. 1, 3 and 4, the guide cannula 5 for the guide wire 50 is coaxially inserted into the guide sleeve 4. The guide cannula 5 is free to slide with friction of the contact surfaces within the guide sleeve 4 performing relative movements of translation along and rotation about the sleeve axis Y. Moreover, the guide cannula 5, being inserted into the guide sleeve 4, will move integrally with the connection rod 11.

The guide cannula 5 has an inner channel which starts from an insertion end 5a up to one outlet end 5b. A handle of the guide cannula 5c is drawn at the insertion end 5a for moving the guide cannula 5.

FIG. 3 shows the whole above-described preferred embodiment of the targeting system 1, applied to a foot skeletal model of a patient with the guide wire 50 inserted in position.

By way of example and with reference to FIG. 3, a possible procedure for applying the targeting system 1 for the insertion of the guide wire 50 at the first metatarsal up to the tarsal of a foot will be briefly described hereafter. The components of the instrument can be assembled, at least partially, before or during the application.

Once the surgeon has identified the point of the bone surface and the insertion direction of the guide wire 50, he will proceed with the application of the targeting instrument 1 so that the outlet end 5b of the guide cannula 5 is located very close to the insertion point of the bone surface and the guide cannula 5 appears to be oriented in the insertion direction.

First, the stabilization body 2 is fixed to the bone by means of the stabilization screws 3, whose distance and relative orientation is adjusted by means of the telescopic structure. The stabilization screws 3 are inserted in specific points of the foot bones so as not to intercept the insertion direction of the guide wire 50 and not to interfere with the cannulated screw inserted then by means of the guide wire 50.

After the insertion of a first stabilization screw 3, it is slidingly inserted into the insertion hole 22 of the first end 20 of the stabilization body 2 and locked by rotating the locking element 28 so as to switch the locking means 23 from the screw sliding configuration to the screw locking one.

After defining the bone point where the second stabilization screw 3 is to be inserted, the telescopic structure is manually adjusted so as to overlap the insertion axis Z of the insertion hole 22 of the second end 21 to the insertion direction of the second stabilization screw 3. The adjustment of the telescopic structure occurs by letting the cylindrical element 30 axially slide and/or rotate about its own axis within the tubular guide element 29.

Once the telescopic structure is adjusted, the second stabilization screw 3 is slidingly inserted into the insertion hole 22 of the second end 21 of the stabilization body 2, screwed to the bone and locked by rotating the locking element 28 so as to switch the locking means 23 from the screw sliding configuration to the screw locking one. The telescopic structure is thereby also locked in position.

Once the stabilization body 2 is fixed to the bone, the guide cannula 5 is positioned in the space by manually adjusting the articulated connection means 6 and the position of the guide cannula 5 within the guide sleeve 4.

The possible adjustments of the articulated connection means 6 available to the surgeon comprise the relative angular movements of the articulated joint 7 and the rotation and the translation of the connection rod 11 with respect to the guide clamp 10.

Once the guide cannula 5 is positioned, the surgeon can insert the guide wire 50 into the insertion end 5a of the guide cannula 5 until it does not come out of the outlet end 5b getting in contact with the bone surface. Then, the surgeon can proceed with the insertion of the guide wire 50 into the bone, by means of a drill, controlling the positioning by radioscopy.

Figure 20:
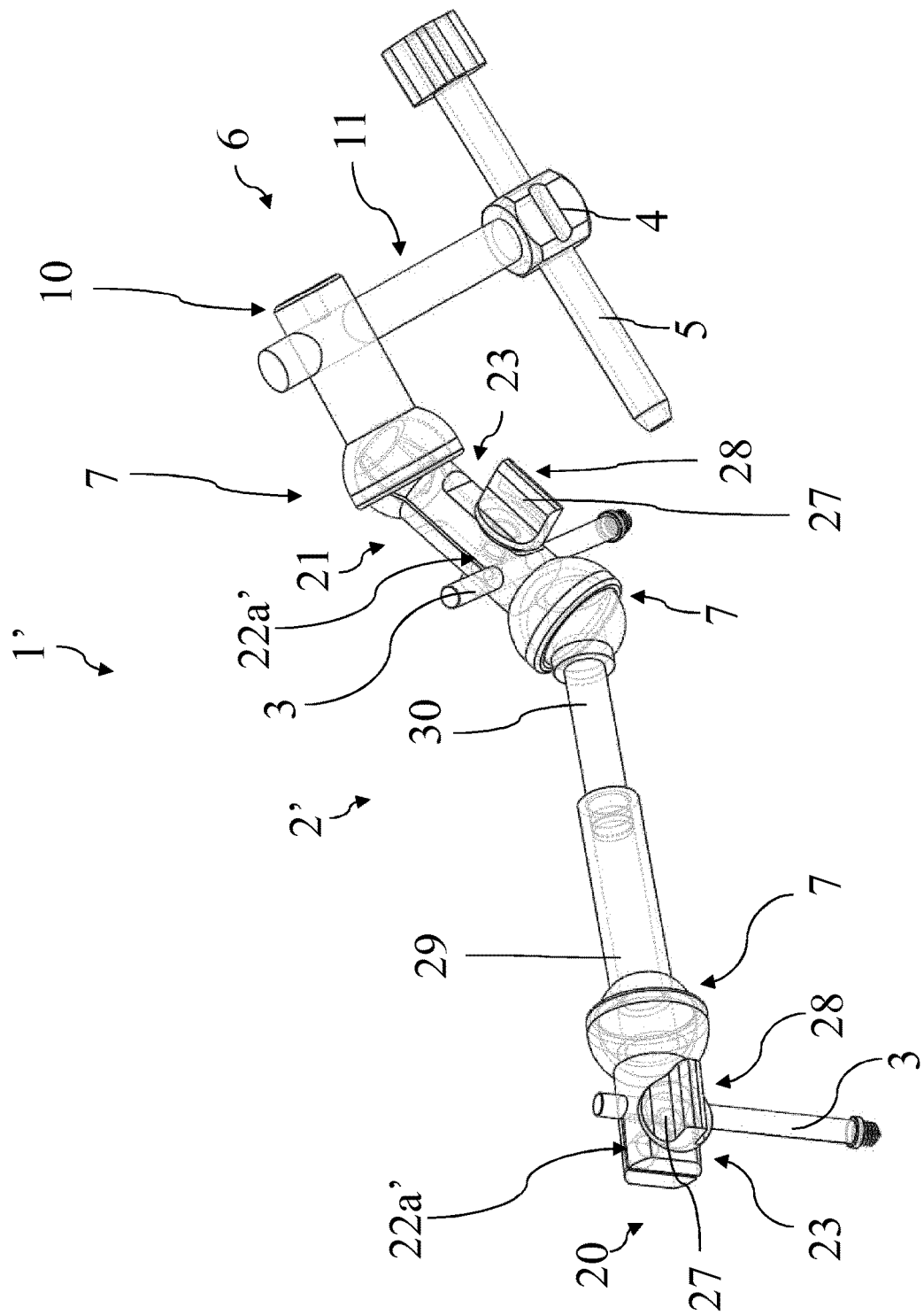
FIG. 20 shows a perspective view of a second embodiment of the targeting system according to the present invention.
Figure 21:
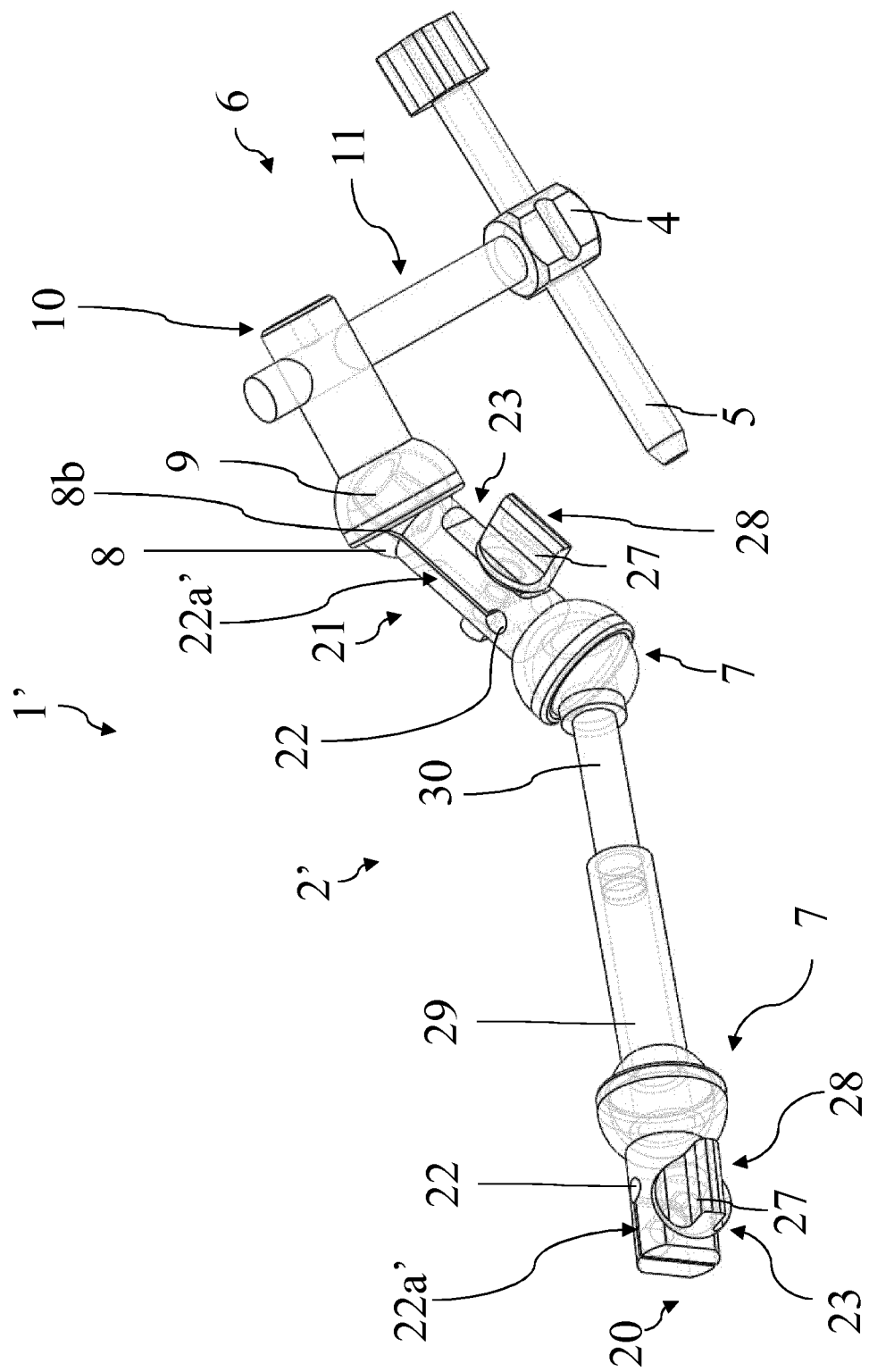
FIG. 21 shows a perspective view of the targeting system of FIG. 20, without stabilization screws inserted.

In FIGS. 20 and 21 an alternative embodiment of the targeting system 1 is indicated with 1'. The differentiating elements are indicated with the superscript '.

In particular, as it is apparent from the above-mentioned figures, the targeting system 1' differs from the targeting system 1 because of the fact that the stabilization body 2' also provides two ball joints 7.

One of the two ball joints 7 of the stabilization body 2' allows the relative angular position between the first end 20, which has the locking means 23 and insertion hole 22 of the stabilization screw 3, and the end of the tubular guide element 29 opposite to the entrance 32 to be varied.

The other of the two ball joints 7 allows on the contrary the relative angular position between the second end 21, which has the locking means 23 and insertion hole 22 of the stabilization screw 3, and the end of the cylindrical element 30 opposite to the insertion end 31 to be varied.

The addition of the two ball joints allows the possible relative angular movements between the stabilization screws 3 to be further increased.

Unlike the previous embodiment, the targeting system 1' further provides a slot 22a' drawn at the first end 20 and the second end 21 of the stabilization body 2' up to lead in the respective insertion hole 22 for the stabilization screw 3. That slot 22a' is arranged according to a plane passing through the insertion hole axis (Z) and orthogonal to the locking hole axis (B).

The slot 22a' defines a first portion 22b' and a second portion 22c' crossed by the locking hole 24 transversely disjoined by the slot 22a'.

The slot 22a' serves to allow the ball joint to be inserted into the complementary seat and the friction to be kept in the movement.

In this second embodiment too, the locking means 23 are of the eccentric type.

Figure 22:
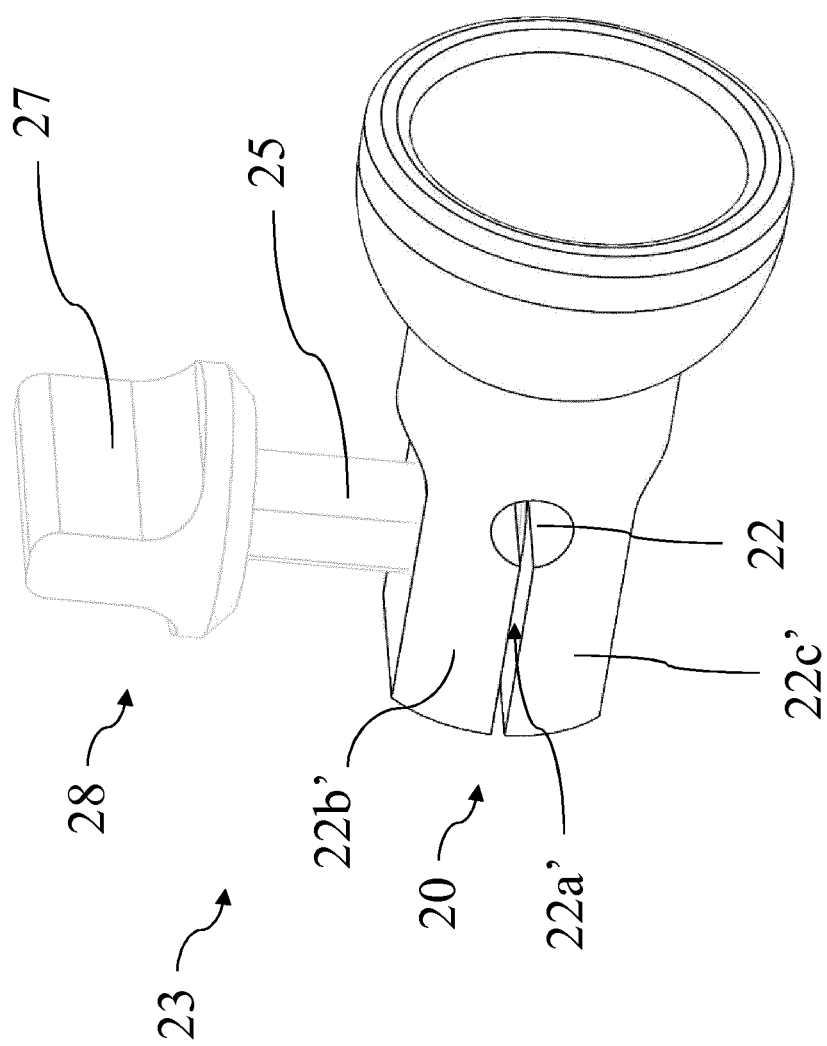
FIG. 22 shows a perspective view of a detail of the locking means of the targeting system of FIG. 20.

FIG. 22 shows a detail of the locking means 23 of the first end 20 of the stabilization body 2'.

Advantageously, the above-described targeting system has a guide cannula to guide the insertion of the guide wire in the point and in the desired direction.

Still advantageously, the guide cannula is connected to a stabilization body fixed to the bone allowing the guide cannula to be kept firmly in position during the guide wire screwing by means of a drill. The position and insertion orientation of the guide wire are univocally defined by the guide cannula and are not biased by possible drill oscillations. This allows the surgeon to work in conditions of higher comfort and safety having a minimum probability to get the wrong positioning of the guide wire.

Still advantageously, the guide cannula slides within a sleeve connected to the stabilization body through articulated connection means which allow the guide cannula to be positioned and oriented in any spatial position and direction. The guide cannula can be thereby advantageously positioned close to the insertion point of the guide wire thus limiting the bending of the guide wire itself during the insertion.

The use of the guide cannula to guide the insertion of the guide wire into the bone further allows the drill to be released from the guide wire in order to be able to control by scopy the wire position without losing the wire positioning and direction.

The targeting system according to the invention solves the technical problem and achieves several advantages, among which that of providing an instrument ensuring a maximum flexibility of use by the surgeon in order to obtain the insertion of the guide wire in the desired position.

The use of means for adjusting the guide cannula position, which can be completely manually operated by the surgeon, without using closing keys, makes the insertion procedure of the guide wire simpler and faster.

The invention claimed is:

1. A targeting system for guided insertion of a guide wire or a bone screw comprising:
   a stabilization body which can be fixed to bone by means of stabilization screws;
   a guide sleeve adapted to receive a guide cannula for insertion of said guide wire or bone screw so that said guide cannula is able to translate along a sleeve axis of said guide sleeve while inserted within said guide sleeve;
   an articulated connector adapted to connect said stabilization body to said guide sleeve and allow a relative spatial position of said guide sleeve to be varied with respect to said stabilizadon body;
   wherein said articulated connector allows at least a relative translation along an axis that is orthogonal to said sleeve axis of said guide sleeve, and
   wherein said stabilization body has, at each of a first and second end, an insertion hole for insertion of a stabilization screw and a locking device for locking said stabilization screw within said insertion hole; said insertion hole being a through hole having an insertion hole axis; said locking device comprises a locking element and a through locking hole having a locking hole axis orthogonal to said insertion hole axis and partially confluent into said insertion hole; said locking element comprising at least one bar adapted to be coaxially introduced into said locking hole; said bar comprising a flattening lying on a plane parallel to said locking hole axis when said bar is inserted into said locking hole; said locking device has a screw locking configuration and a screw sliding configuration; in the screw sliding configuration, said bar is inserted into said locking hole with said flattening parallel to said insertion hole axis and facing said stabilization screw in such a way that said stabilization screw is freely slidable within said insertion hole; in the screw locking configuration, said bar is in a rotated position with respect to the screw sliding configuration and interfering with said stabilization screw which is thereby locked within said insertion hole.

2. The targeting system according to claim 1, wherein said stabilization body comprises a telescopic structure adapted to vary a distance and a relative orientation between said stabilization screws inserted into said insertion holes.

3. The targeting system according to claim 2, wherein said telescopic structure comprises a tubular guide element integral with one of said first and second ends and a cylindrical element integral with the other of said first and second ends; said cylindrical element being at least partially coaxially inserted into said tubular guide element; said cylindrical element being free to slide and rotate about its own axis while at least partially inserted within said tubular guide element, approaching/moving away and/or rotating said stabilization screws with respect to each other.

4. The targeting system according to claim 3, wherein said cylindrical element has an insertion end adapted to be press-fitted into an entrance of said tubular guide element; said entrance having a projection of an inner wall which determines a local reduction of an inner diameter; said insertion end comprising a shoulder which determines a localized extension of a diameter of said cylindrical element; said shoulder being arranged to be located in abutment against said projection in order to prevent a decoupling of said cylindrical element from said tubular guide element.

* * * * *

UNITED STATES PATENT AND TRADEMARK OFFICE
CERTIFICATE OF CORRECTION

PATENT NO. : 11,090,065 B2
APPLICATION NO. : 16/609896
DATED : August 17, 2021
INVENTOR(S) : Federico Vicenzi It is certified that error appears in the above-identified patent and that said Letters Patent is hereby corrected as shown below:

In the Claims

In Column 10, Line 4, Claim 1:
"stabilizadon" should be -- stabilization --

Signed and Sealed this
Twenty-sixth Day of April, 2022

*Katherine Kelly Vidal*

Katherine Kelly Vidal
*Director of the United States Patent and Trademark Office*